(12) United States Patent
Gabetta et al.

(10) Patent No.: US 9,133,152 B2
(45) Date of Patent: *Sep. 15, 2015

(54) PROCESS FOR THE PURIFICATION 10-DEACETYLBACCATINE III FROM 10-DEACETYL-2-DEBENZOYL-2-PENTENOYLBACCATINE III

(75) Inventors: Bruno Gabetta, Milan (IT); Andrea Gambini, Milan (IT)

(73) Assignee: INDENA S.P.A., Milan (IT)

( * ) Notice: Subject to any disclaimer, the term of this patent is extended or adjusted under 35 U.S.C. 154(b) by 1752 days.

This patent is subject to a terminal disclaimer.

(21) Appl. No.: 11/918,283

(22) PCT Filed: Apr. 7, 2006

(86) PCT No.: PCT/EP2006/003162
§ 371 (c)(1),
(2), (4) Date: Jan. 21, 2009

(87) PCT Pub. No.: WO2006/108561
PCT Pub. Date: Oct. 19, 2006

(65) Prior Publication Data
US 2009/0298926 A1    Dec. 3, 2009

(30) Foreign Application Priority Data
Apr. 12, 2005   (IT) .............................. MI2005A0614

(51) Int. Cl.
*C07D 305/14*   (2006.01)
(52) U.S. Cl.
CPC .................................. *C07D 305/14* (2013.01)

(58) Field of Classification Search
CPC ..................................................... C07D 305/14
See application file for complete search history.

(56) References Cited

U.S. PATENT DOCUMENTS

| 5,453,520 | A  | * | 9/1995 | Bombardelli et al. | 549/510 |
| 6,737,534 | B2 | * | 5/2004 | Pontiroli et al. | 549/296 |
| 2004/0049060 | A1 | * | 3/2004 | Battaglia et al. | 549/510 |
| 2006/0079571 | A1 |  | 4/2006 | Gabetta et al. | |

FOREIGN PATENT DOCUMENTS

| WO | WO 00/52003 A1 | 9/2000 |
| WO | WO 02/12215 A1 | 2/2002 |
| WO | WO 02/44161 A2 | 6/2002 |

OTHER PUBLICATIONS

Vogel, (Practical Organic Chemistry, 3rd Ed. (1956), Longman Group London, p. 156-163).*
Gueritte-Voegelein et al. (Tetrahedron (1986), 42(16); p. 4451-4460).*
Gabetta et al., "10-Deacetylbaccatin III Analogues From *Taxus baccata*l", J Nat Prods 58 (10):1508-1514 (1995).

* cited by examiner

*Primary Examiner* — Valerie Rodriguez-Garcia
(74) *Attorney, Agent, or Firm* — Porzio, Bromberg & Newman, P.C.

(57) ABSTRACT

A process for the preparation of 10-deacetyl-7,10-bis-trichloroacetylbaccatine III with HPLC purity higher than 99% and free from 2-debenzoyl-2-pentenoylbaccatine III by purification of 10-deacetyl-7,10-bis-trichloroacetylbaccatineIII followed by alkaline hydrolysis of the protecting groups in position 7 and 10.

4 Claims, No Drawings

PROCESS FOR THE PURIFICATION 10-DEACETYLBACCATINE III FROM 10-DEACETYL-2-DEBENZOYL-2-PENTENOYLBACCATINE III

The present invention relates to the preparation of 10-deacetylbaccatine III free from 10-deacetyl-2-debenzoyl-2-pentenoylbaccatine III.

The removal of this impurity is carried out by transforming 10-deacetylbaccatine III into the corresponding 7,10-bis-trichloroacetate, followed by chromatographic purification and de-blocking of the hydroxy groups. The 10-deacetylbaccatine III purified according to this method can be conveniently used for the semi-synthesis of antitumor medicaments with taxane skeleton, avoiding troublesome purifications from the corresponding 2-debenzoyl-2-pentenoyl analogues.

INTRODUCTION

10-Deacetylbaccatine III (I) is the starting product for the semi-synthesis of medicaments with potent antitumor activity, such as docetaxel and paclitaxel. 10-Deacetylbaccatine III is isolated by extraction from plants of the *Taxus* genus. The extraction product also contains a variable amount of related compounds (see table), which depend on the origin of the plant material. In general, the impurities contained in commercially available 10-deacetylbaccatine III have a further hydroxy group at the 14- or 19-position or have an opposite configuration at the 7- and 13-position.

Other impurities are substituted at the 13-position with a phenylisoserine residue, whose amine function is linked to a propionic, butyric, tiglic or benzoic residue. Moreover, 10-deacetylbaccatine III contains a further metabolite (II) which, instead of a benzoyl function at the 2-position, carries a pentenoyl residue, identified in particular as a tiglic acid residue (B. Gabetta et al., J. Nat. Prod. 58, 1508, 1995). Usually this impurity, which cannot be removed through crystallization due to its tendency to co-crystallize with 10-deacetylbaccatine III, is contained in amounts of 0.3-1% in commercial 10-deacetylbaccatine III. Moreover, costly chromatographic purifications allow only partial and unsatisfactory reduction of its content.

When an antitumour drug is prepared from 10-deacetylbaccatine III, this impurity undergoes the same semi-synthesis process as 10-deacetylbaccatine III, giving rise to the corresponding 2-debenzoyl-2-pentenoyl derivative, whose removal is extremely troublesome.

For this reason, for example, the American pharmacopoeia allows the presence of relevant amounts (up to 0.7%) of 2-debenzoyl-2-pentenoylpaclitaxel in semi-synthetic paclitaxel.

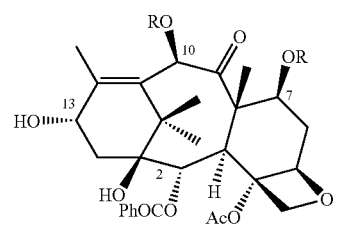

(I) R = H
(III) R = CCl$_3$CO

TABLE

Main impurities contained in commercial 10-deacetylbaccatine

| | $R_1$ | $R_2$ | $R_3$ | $R_4$ | $R_5$ |
|---|---|---|---|---|---|
| Ia | Bz | β-OH | OH | α-OH | H |
| Ib | Bz | α-OH | OH | α-OH | H |
| Ic | Bz | β-OH | H | β-OH | H |
| Id | Bz | β-OH | H | α-OH | OH |
| Ie | Bz | α-OH | H | α-OH | H |
| II | Tigl | β-OH | H | α-OH | H |

| | $R_6$ |
|---|---|
| Ia | EtCO |
| Ib | PrCO |
| Ic | Tigl |
| Id | Bz |

Bz =

Tigl =

DISCLOSURE OF THE INVENTION

The present invention relates to a process for the purification of 10-deacetylbaccatine III from 10-deacetyl-2-debenzoyl-2-pentenoylbaccatine III (II), wherein the pentenoyl residue is a tiglic acid residue. Therefore, 10-deacetylbaccatine III purified according to the invention allows to obtain antitumor medicaments with taxane sketeton free from the corresponding impurities having a pentenoyl residue instead of a benzoyl residue at the 2-position.

10-Deacetylbaccatine III can be easily transformed into the 7,10-bis-trichloroacetyl derivative (III). The conversion can be carried out by treatment with trichloroacetic acid activated derivatives, according to known esterification methods. Preferably, III is obtained by reaction with trichloroacetyl chloride at a temperature of about 0° C., preferably of −5 to +5° C., using pyridine or a pyridine-dichloromethane mixture as the solvent. HPLC analysis shows that (III) contains, as impurities, about 2% of the corresponding 10- and 7-monoacylated products, as well as impurity (II) 7,10-bis-trichloroacetate, in amount proportional to that of (II) in the 10-deacetylbaccatine III used as the starting material.

It has surprisingly been found that the bis-trichloroacetyl derivative of the latter impurity (II) has a markedly different chromatographic behaviour from that of bis-trichloroacetyl 10-deacetylbaccatine III (III).

In fact, when the trichloroacetylation products are subjected to column chromatography on small amounts of silica gel, preferably 10-20 parts by weight, more preferably 15 parts by weight, and eluted with dichloromethane or a dichloromethane-ethylacetate mixture, 7,10-bis-trichloroacetyl 10-deacetylbaccatine III (III) is eluted, whereas the corresponding 2-debenzoyl-2-pentenoyl analogue is retained on the stationary phase together with monoacylated products. These impurities can be recovered using a solvent with higher polarity than dichloromethane, for example acetone or methanol.

The resulting 7,10-bis-trichloroacetylbaccatine III (III) can be used as such for the semi-synthesis of antitumor medicaments by esterification of the 13-position with a suitably activated side chain. Therefore, the use of derivative III, obtained with a chromatographic purity higher than 99%, is a further embodiment of the invention. Indeed, its advantage consists in the presence of trichloroacetyl protective groups at both the 7- and 10-position, further to the absence of the 2-debenzoyl-2-pentenoyl analogue. This avoids further and undesired esterifications at the 7- and/or 10-positions with the selected side chain, and the formation of impurities which could not otherwise be easily removed. Therefore, esterification of the 13-position with a suitable side chain followed by removal of the protective groups from the 7- and 10-position and from the side chain allows to obtain docetaxel or its precursors (having a suitable protected side chain) free from di(phenylisoserinyl)-analogues.

On the other hand, 10-deacetylbaccatine III free from the 2-debenzoyl-2-pentenoyl analogue and other impurities can be regenerated from product (III), (purified as described above) through alkaline treatment, preferably by reaction with ammonium hydroxide in a suitable solvent, such as methanol, or a methanol-dichloromethane mixture or tetrahydrofuran. By crystallization from a suitable solvent, such as acetonitrile, acetone or methanol, 10-deacetylbaccatine III is obtained with chromatographic purity higher than 99% and free from compound (II) as impurity.

Therefore, the resulting 10-deacetylbaccatine III obtained can be conveniently used for the preparation of semi-synthetic paclitaxel free from 2-debenzoyl-2-pentenoyl-paclitaxel. Paclitaxel can be obtained by means of any method which allows to transform 10-deacetylbaccatine III into N-debenzoylpaclitaxel, followed by benzoylation. A convenient method for the preparation of N-debenzoylpaclitaxel is disclosed for example in US 20050049297.

A further object of the invention is therefore semi-synthetic paclitaxel free from 2-debenzoyl-2-pentenoyl-paclitaxel and pharmaceutical compositions containing thereof.

The invention is illustrated in greater detail in the examples reported below.

Example 1—10-Deacetyl-7,10-bistrichloroacetylbaccatine III (III)

10-Deacetylbaccatine III (15 g), containing 0.4% of 2-debenzoyl-2-pentenoyl analogue as impurity, is treated with 6.6 ml of trichloroacetyl chloride in 60 ml of pyridine at 0-5° C. for one hour under stirring. The mixture is diluted with 100 ml of methylene chloride and 100 ml of 4 N hydrochloric acid. The phases are separated and the organic one is washed with 100 ml of 4 N hydrochloric acid and then with 500 ml of water saturated with sodium chloride. The organic phase is concentrated to dryness and the residue is taken up with 100 ml of toluene. The solid (24.9 g) is recovered by filtration, re-dissolved in 125 ml of methylene chloride and purified by column chromatography on 375 g of Kieselgel 60 Merck, eluting with methylene chloride. The fractions that contain III are collected and added with toluene; the resulting precipitate is filtered off and dried under vacuum at 50° C., giving 17.8 g of III with HPLC purity higher than 99%. HPLC-MS analysis does not show the presence of (II) bis-trichloroacetate.

Example 2—10-Deacetylbaccatine III Free from 2-debenzoyl-2-pentenoyl Analogue

10-Deacetyl-7,10-bis-trichloroacetylbaccatine III (17.8 g), obtained as described in example 1, is dissolved under inert atmosphere in 36 ml of tetrahydrofuran and treated under stirring for thirty minutes with 3.9 ml of concentrated ammonium hydroxide. The solution is diluted with acetonitrile and then concentrated until incipient crystallization, thereafter the product is filtered and recrystallized from acetone, to give 10 g of 10-deacetylbaccatine III with HPLC purity higher than 99% and free from 2-debenzoyl-2-pentenoylbaccatine III.

Example 3—Paclitaxel Free from 2-debenzoyl-2-pentenoyl Analogue

N-Debenzoylpaclitaxel (700 g) is prepared as described in examples V-VII of US 2005/0049297 A1, starting from 10-DAB III purified according to Example 2 above (therefore free from the 2-debenzoyl-2-pentenoyl analogue), thereafter is dissolved in 14 l of acetonitrile, added with 120 ml of triethylamine and treated with 107 ml of benzoyl chloride.

The reaction mixture is stirred at room temperature for half an hour and diluted with 21 l of water containing 0.1% of acetic acid.

The solid material is filtered, washed with 3 l of a 3:2 water-acetonitrile mixture and dried under vacuum at 50° C. About 700 g of dry solid material are obtained, from which, by crystallization from 2:1 cyclohexane-acetone and drying under vacuum, 600 g of paclitaxel free from 2-debenzoyl-2-pentenoylpaclitaxel are obtained.

The invention claimed is:

1. A process for the preparation of 10-deacetylbaccatine III with a purity higher than 99% and free from 2-debenzoyl-2-pentenoylbaccatine III by submitting 7,10-bis-trichloroacetyl-10-deacetylbaccatine III to alkaline treatment followed by crystallization wherein the crystallization of 10-deacetylbaccatine III is carried out with a solvent selected from acetonitrile, acetone or methanol; and wherein the 7,10-bis-trichloroacetyl-10-deacetylbaccatine III is prepared by the process of:
   treatment of crude 10-deacetylbaccatine III with a trichloroacetic acid activated derivative; and silica gel chromatography and elution of 7,10-bis-trichloroacetyl-10-deacetylbaccatine III with dichloromethane or a dichloromethane-ethylacetate mixture.

2. The process as claimed in claim 1 in which the alkaline treatment is carried out by reaction with ammonium hydroxide in a solvent selected from methanol, a methanol-dichloromethane mixture or tetrahydrofuran.

3. The process as claimed in claim 1 in which treatment of crude 10-deacetylbaccatine III with a trichloroacetic acid activated derivative is carried out at a temperature of −5° C. to +5° C. in pyridine or in a pyridine-dichloromethane mixture.

4. The process as claimed in claim 1 in which the silica gel chromatography is carried out using from 10 to 20 parts by weight of silica gel with respect to the weight of the 7,10-bis-trichloroacetyl-10-deacetylbaccatine III.

* * * * *